(12) United States Patent
Bar-Tana

(10) Patent No.: US 6,284,903 B1
(45) Date of Patent: Sep. 4, 2001

(54) CARBOXYLIC ACIDS AND DERIVATIVES THEREOF AND PHARMACEUTICAL COMPOSITIONS CONTAINING THEM

(75) Inventor: Jacob Bar-Tana, Jerusalem (IL)

(73) Assignee: Yissum Research Development Co. of the Hebrew University of Jerusalem, Jerusalem (IL)

(*) Notice: Subject to any disclaimer, the term of this patent is extended or adjusted under 35 U.S.C. 154(b) by 0 days.

(21) Appl. No.: 09/331,895

(22) PCT Filed: Dec. 25, 1997

(86) PCT No.: PCT/IL97/00427

§ 371 Date: Oct. 5, 1999

§ 102(e) Date: Oct. 5, 1999

(87) PCT Pub. No.: WO98/30530

PCT Pub. Date: Jul. 16, 1999

(30) Foreign Application Priority Data

Jan. 7, 1997 (IL) .......................................... 119971

(51) Int. Cl.$^7$ .................................................. C07C 59/235
(52) U.S. Cl. ............................................ 554/121; 514/547
(58) Field of Search ............................... 554/121; 514/547

(56) References Cited

U.S. PATENT DOCUMENTS

| 3,930,024 | * | 12/1975 | Creger . |
| 4,634,795 | * | 1/1987 | Bar-Tana . |
| 4,666,895 | * | 5/1987 | Bosies et al. . |
| 4,689,344 | * | 8/1987 | Bar-Tana . |
| 4,711,896 | * | 12/1987 | Bar-Tana et al. . |
| 5,641,810 | * | 6/1997 | Pill et al. . |

FOREIGN PATENT DOCUMENTS

| 4224670 | * | 1/1994 | (DE) . |
| 2288516A | | 5/1976 | (FR) . |
| 35200 | * | 8/1970 | (IL) . |
| 84107 | * | 3/1988 | (IL) . |
| 96 30328 | | 10/1996 | (WO) . |

OTHER PUBLICATIONS

ACS Chem. Abstr. Tryding, vol. 51, No. 22, Nov. 25, 1957, 1975.*
Newkome et al. Chem. Abstr., 83:178236, 1975.*
Borgen et al, Chem. Abstr., 77:61278, 1972.*
Bjornstad et al., Chem. Abstr., 82:155110, 1975.*
Nelson et al., JOACS, vol. 72, No. 11, pp. 5388–5397, especially 5390–5391, 1950.*
Database CA on STN, No. 77:61278, Borgen et al. 'Synthesis of bis (gem–dimethyl) cycloalkanones and tetraks (gem–dimeththyl) cycloalkanediones.' abstract, Acta Chem. Scand., 1972.*
Database CA on STN, No. 82:155110, Bjornstad et al. 'Bis (gem–dimethyl)–substituted cylic diynes,' abstract, Acta Chem. Scand. Ser. B. 1975.*
Nelson et al. The Influence of Steric Configuration of the Ultraviolet Absorption of 1,2–Diketones. Journal of the American Chemical Society. Nov. 1950. vol. 72. No. 11. pp 5388–5397, especially pp. 5390–5391.*
The American Chemical Society 'Chemical Abstracts Tryding', vol. 51 No. 22, Nov. 25, 1957.*

* cited by examiner

Primary Examiner—Deborah D. Carr
(74) Attorney, Agent, or Firm—Eitan, Pearl, Latzer & Cohen-Zedek

(57) ABSTRACT

The present invention relates to a novel class of compounds for treating hyperlipidemia, obesity and impaired glucose tolerance/noninsulin dependent diabetes mellitus without adversely affecting energy metabolism, and pharmaceutical compositions comprising the aforementioned compounds for the treatment of obesity, hyperlipidemia and maturity-onset diabetes.

10 Claims, 1 Drawing Sheet

US 6,284,903 B1

Figure 1:
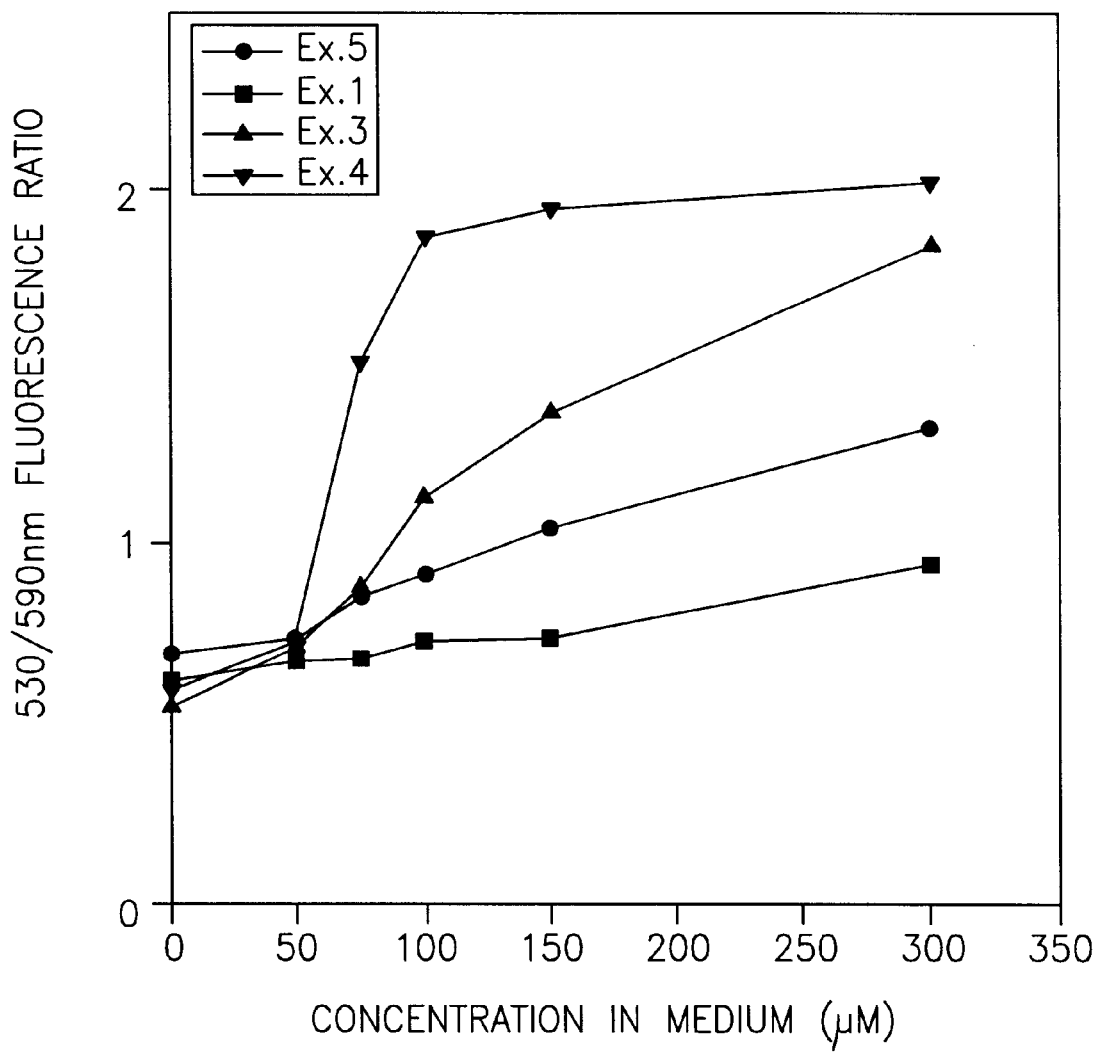

CARBOXYLIC ACIDS AND DERIVATIVES THEREOF AND PHARMACEUTICAL COMPOSITIONS CONTAINING THEM

This application is a 371 of PCT/IL97/00427 filed Dec. 25, 1997.

FIELD OF INVENTION

A novel class of compounds has been found to be effective in treating hyperlipidemia, obesity and impaired glucose tolerance/noninsulin dependent diabetes mellitus without adversely affecting energy metabolism. The active compounds have the general formula

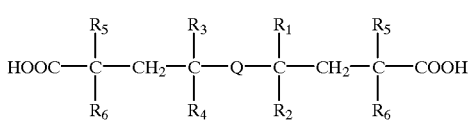

(I)

$R_1$–$R_4$ each independently represents a hydrogen or an unsubstituted or substituted hydrocarbyl or heterocyclyl radical;

where $R_5$ and $R_6$ independently represent hydrogen, hydroxyl, lower alkyl, chloro, bromo, cyano, nitro, lower alkoxy, or trifluoromethyl Q represents a diradical consisting of a linear chain of 2 to 14 carbon atoms, one or more of which may be replaced by heteroatoms, said chain being optionally substituted by inert substituents and one or more of said carbon or heteroatom chain members optionally forming part of a ring structure and where one or both of the carboxyl groups can be substituted by an in vivo hydrolyzable physiologically acceptable substituent.

The invention also provides pharmaceutical compositions comprising the aforementioned compounds of formula (I) for the treatment of obesity, hyperlipidemia and maturity-onset diabetes.

BACKGROUND OF THE INVENTION

Dyslipoproteinemia (combined hypercholesterolemia-hypertriglyceridemia), low HDL-cholesterol), obesity (in particular upper body obesity), impaired glucose tolerance (IGT) leading to noninsulin-dependent *diabetes mellitus* (NIDDM)) and essential hypertension are common diseases that afflict individuals living in Westernized societies. Being initiated and linked through hyper-insulinemia these four diseases often coexist and precipitate independently as well as synergistically atherosclerotic vascular disease leading to coronary heart disease. The incidence of the Deadly Quartet (Syndrome-X, Metabolic Syndrome) comprising the four diseases increases as the population ages and by 70 years of age reaches epidemic proportions. Combatting the individual categories of the Deadly Quartet as well as offering a whollystic therapeutic approach to the Syndrome is considered one of the most important challenges of medicine in affluent Westernized society.

Many hypercholesterolemic/hypertriglyceridemic individuals turn out as low- or non-responders to dietary measures and therefore are candidates for long-term treatment with hypolipidemic drugs. HMG-CoA reductase inhibitors and bile acid sequestrants designed to upregulate the LDL receptor are very effective in isolated hyper-cholesterolemia. However, both are ineffective in reducing plasma triglycerides and poorly effective in increasing plasma HDL, thus being short of offering an adequate treatment mode for combined hypertriglyceridemia-hypercholesterolemia (which comprise of >70% of dyslipoproteinemic patients) or for isolated hypertriglyceridemia with reduced plasma HDL, as well as for the postprandial chylomicrons-rich phase realized now as an independent risk for atherosclerotic cardiovascular disease. Isolated hyper-triglyceridemia may however be treated with either nicotinic acid or drugs of the fibrate family. However, the compliance for nicotinic acid is very poor and the advantage of fibrate drugs in lowering overall mortality has been seriously questioned since the exhaustive WHO clofibrate study. Also, nicotinic acid is ineffective while fibrate drugs are only poorly effective in reducing plasma cholesterol, thus leaving the combined hypertriglyceridemic-hypercholesterolemic patient with the only choice of a combination treatment mode (e.g., HMG-CoA reductase inhibitor/nicotinic acid). Weight reduction measures are essentially based on promoting dietary or behavioral means for reducing weight. However, most obese individuals turn out to respond inadequately to dietary or behavioral measures, especially if examined over long time periods. The chances for 5-year maintenance of weight reduction initiated by dietary and behavior modifications are less than 10%. This overwhelming failure is mainly metabolic, since the decrease in weight as a result of dieting is always accompanied by a decrease in basal metabolic rate and overall energy expenditure, thus forcing the dieting obese patient into a genuine deadlock. Antiobesity drugs based on modulating energy intake are currently based on anorectics designed to depress the hypothalamic satiety center. These drugs are reported to be ineffective in the medium and long range and some may induce primary pulmonary hypertension. Similarly, no antiobesity drugs are presently available based on modulating total body calorie expenditure while allowing free access to calorie consumption. Peripherally acting thermogenic β3-adrenergic agonists are selected on the basis of their capacity to stimulate brown adipose tissue β-adreno receptors and may indeed induce thermogenesis in rodents. However, the efficacy of such agents in humans while allowing free access to calories is still questionable and their ;broad tissue specificity (e.g., skeletal muscle, myocardium, colon) may be expected to result in nonspecific-adrenergic-induced effects.

Presently available pharmacological measures for treating IGT and overt NIDDM consist of two oral hypoglycemic drug types which are in use for over 30 years. The sulphonylureas promote pancreatic insulin secretion for coping with peripheral insulin resistance, while biguanides are claimed to improve peripheral insulin action. The popularity of sulphonylurea does result from the old conviction that blood glucose which precipitates the diabetic microvascular disease in retina kidney, nerve and some other tissues should be normalized by all means even at the expense of increased pancreatic insulin secretion. This therapeutic approach was initiated in times when the hyperinsulinemic phase dominating the natural history of the development of NIDDM or the course of obesity-induced IGT was not realized, neither the pathological sequel dictated by sustained hyperinsulinemia. Moreover, the sulphonylurea (similarly to insulin) tend to promote weight gain, thus further promoting insulin resistance and compensatory hyperinsulinemia leading to diabetes-induced macrovascular disease (atherosclerotic cardiovascular disease). Biguanides are claimed to potentiate insulin-mediated glucose disposal with no stimulation of pancreatic insulin secretion. However, the use of biguanides as monotherapy is not unanimously recommended except for the very obese in light of their low therapeutic/toxicity index and the induction of lactic acidosis. During the period of the last ten years, the scientific community became progressively aware of the etiological-pathophysiological linkage between dyslipo-proteinemia, obesity, NIDDM, hypertension, decreased fibrinolysis and some other pathologies (e.g., hyperuricemia), realizing now that the concerned pathologies are just reflections of a unifying Syndrome. Leading to atherosclerotic cardiovascular disease, the Syndrome is realized now to be the major risk factor for mortality and morbidity in Western Societies. Treating the Syndrome pharmacologically calls for an whollystic approach rather than dealing separately with each of its distinct categories. No drug designed alongside these principles is yet available.

α, ω-Dialkanoic acids of chain length of 14 20 carbon atoms which are hydrocarbyl substituted on the β,β' carbon atoms, as well as their salts and ester derivatives were disclosed in Bar-Tana U.S. Pat. Nos. 4,634,795, 4,689,344 and 4,711,896 as possessing a hypolipidemic, weight reducing and antidiabetogenic activity. Realizing however that treatment of the Metabolic Syndrome and its related pathologies would require chronic dosing has initiated an exhaustive search for new compounds having a higher efficacy as compared with the previously disclosed β,β'-substituted α,ω dialkanoic acids.

DESCRIPTION OF THE INVENTION

A novel class of compounds has now been found, in accordance with the present invention, to be surprisingly effective in reducing blood lipids. The new compounds of the invention were also found to have a calorigenic antidiabetic (NIDDM) activity without adversely affecting energy metabolism. Furthermore, the efficacy of some of these compounds is far better as compared with previously reported β,β'-substituted α,ω-dialkanoic acids. The novel compounds provided by the present invention are α,ω-dialkanoic acids having the general formula

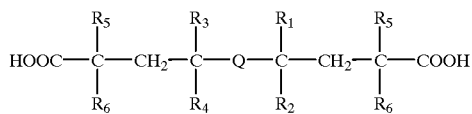

and in vivo hydrolysable functional derivatives of the carboxylic groups thereof, wherein $R_1$–$R_4$ each independently represents a hydrogen or an unsubstituted or substituted hydrocarbyl;

where $R_5$ and $R_6$ independently represent hydrogen, hydroxyl, lower alkyl, chloro, bromo, cyano, nitro, lower alkoxy, or trifluoromethyl;

Q represents a diradical consisting of a liner chain of 2 to 14 carbon atoms, one or more of which may be replaced by heteroatoms, said chain being optionally substituted by inert substituents qnid one or more of said carbon or heteroatom chain members optionally forming part of a ring structure.

Included within the scope of the invention are those derivatives of the α and/or ω carboxy groups of the compounds of formula I above, which are capable of being hydrolyzed in vivo to yield the free diacids of formula I. Among such suitable derivatives there should be mentioned. in the first place salts with pharmaceutically acceptable inorganic or organic cations, in particular alkali metal salts, alkaline earth metal salts, ammonium salts and substituted ammonium salts; esters, particularly lower alkyl esters; amides, mono- and di-substituted amides; and anhydrides, e.g., with lower alkanoic acids; and lactones formed by ring closure of either or both carboxylic groups with a free hydroxy substituent (or substituents) in the molecule of formula (I).

The term "hydrocarbyl" in the definition of $R_1$–$R_4$ includes, e.g., optionally substituted alkyl, alkenyl, alkynyl, cycloalkyl, optionally substituted aryl, optionally substituted aralkyl and the like.

A preferred group of compounds in accordance with the invention are those of formula (I) above in which $R_1$–$R_4$ are each lower alkyl and Q is a straight polymethylene chain of 2 to 14 carbon atoms; and in vivo hydrolysable functional derivatives thereof.

Especially preferred compounds of the present invention are those of the general formula

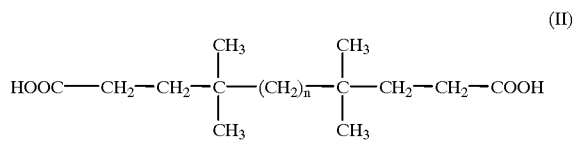

and their in vivo hydrolysable functional derivatives, wherein n is an integer from 6 to 12;
or of the general formula

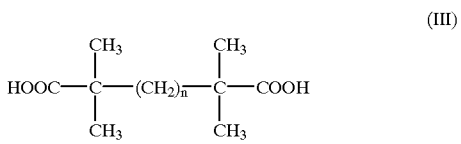

where n is an integer from 10–16; and their in vivo hydrolyzable function derivatives.

The novel compounds of formula (I) according to the invention, can be prepared by methods knownper se, some of which are illustrated in the examples herein.

In another aspect, the present invention provides pharmaceutical compositions for the treatment of obesity, hyperlipidemia, diabetes or the Metabolic Syndrome, comprising as active ingredients the novel compounds of formula (I) above together with pharmaceutical carriers or diluents. The pharmaceutical compositions are primarily for oral administration, but may also be for parenteral or topical administration. These pharmaceutical compositions, which are preferably in dosage unit form, may be in the form of, e.g., tablets, capsules, lozenges, pills, powders and aqueous and non-aqueous solutions or suspensions. The pharmaceutical compositions of this invention preferably comprise also conventional pharmaceutical solid or liquid carriers or diluents, e.g., gelatin, sugars, starches, cellulose derivatives, fatty acids and their salts, vegetable oils, glycerine, glycols, water, aqueous saline or phosphate buffer solutions and the like. The compositions may also comprise other compatible substances normally used in pharmaceutical formulations and also other additives, such as colouring agents, flavouring agents and preservatives.

The pharmaceutical compositions according to the invention are preferably in dosage unit form, each unit containing from 50 to 500 mg of the active ingredient of the formula (I) above. The daily dosage of the compounds of formula (I) above according to the invention will depend on the age, needs and tolerance of the individual patient, but will usually range from 50 mg to from 5,000 mg per day.

The pharmacological activities of the compounds of formula (I) according to the invention could be demonstrated by means of in vivo experiments in rats and in vitro experiments in liver cells in accordance with standard methods. Some of these experiments are described hereinafter in detail.

EXPERIMENTS IN RATS IN VIVO AND IN LIVER CELLS

EXPERMN I

Rats (n=5 for each treatment group) were fed ad libitum on Purina chow for 6 days, the diet being supplemented with 0.1% (w/w) $\gamma,\gamma'$-methyl substituted $\alpha,\omega$-dioic acids of formula (II) (Ex. 1, Ex. 3, Ex. 4) in the diet. The biological effect in vivo was evaluated by following food intake, plasma triglycerides, plasma cholesterol and plasma glucose. The results are shown in the following Table I.

TABLE I

|  | Nontreated | Ex. 1 | Ex. 3 | Ex. 4 |
|---|---|---|---|---|
| Plasma triglycerides (mg %) | 63.9 ± 24.1 | 24.8 ± 3.9 | 28.8 ± 7.4 | 29.3 ± 10.4 |
| Plasma cholesterol (mg %) | 66.3 ± 5.6 | 64.1 ± 12.0 | 62.4 ± 13.3 | 56.8 ± 10.8 |
| Plasma glucose (mg %) | 141.2 ± 10.7 | 127.8 ± 6.6 | 138.8 ± 2.7 | 139.0 ± 9.0 |
| Food intake (g/d) | 19.1 ± 1.7 | 18.6 ± 2.1 | 19.3 ± 1.1 | 19.1 ± 1.2 |

EXPERIMENT II

Rats (n=5 for each treatment group) were fed ad libitum on purina chow for 5 days, the diet being supplemented with either $\gamma,\gamma'$-methyl substituted $\alpha,\omega$ hexadecanedioic acid (formula (II), Ex. 3) or $\beta,\beta'$-methyl substituted $\alpha,\omega$-hexadecanedioic acid (U.S. Pat. No. 4,634,795) at a dosage of 0.09% (w/w) in the diet. The biological effect in vivo was evaluated by following plasma triglycerides, plasma apolipoprotein(apo)C-III, plasma insulin and the steady state concentrations (Css) of the respective drugs in plasma. Fold efficacy of the $\gamma,\gamma'$-sbstituted compound (Ex. 3) relative to the $\beta,\beta'$-substituted compound was calculated by normalizing the observed effect by the respective Css attained. The results are shown in the following Table II.

TABLE II

|  | Nontreated | $\beta,\beta'$-methyl-hexadecane $\alpha,\omega$-dioic acid | $\gamma,\gamma'$-methyl-hexadecane $\alpha,\omega$-dioic acid (Ex.3) | Fold efficacy ($\gamma,\gamma/\beta,\beta$) |
|---|---|---|---|---|
| Plasma triglycerides (mg %) | 61.0 ± 13.5 | 19.7 ± 4.0 | 19.9 ± 7.4 | 8.2 |
| Plasma apo C-III (mg %) | 33.0 ± 10.0 | 11.0 ± 3.7 | 12.0 ± 4.6 | 7.7 |
| Plasma insulin (U/ml) | 31.0 ± 6.5 | 23.0 ± 3.4 | 16.0 ± 6.1 | 15.2 |
| Css (g/ml) |  | 97.4 ± 12.6 | 12.0 ± 1.2 |  |

EXPERIMENT III

Conditions as in EXPERIMENT II using $\alpha,\alpha'$-methyl-substituted $\alpha,\omega$-tetradecanedioic acid. The results are shown in the following Table III.

Fold efficacy represents the respective effect induced by the $\alpha,\alpha'$-substituted compound (Ex. 5) relative to that of the $\beta,\beta'$-substituted compound.

TABLE III

|  | Nontreated | $\beta,\beta'$-methyl-hexadecane $\alpha,\omega$-dioic acid | $\alpha,\alpha'$-methyl-hexadecane $\alpha,\omega$-dioic acid (Ex.6) | Fold efficacy |
|---|---|---|---|---|
| Plasma Triglycerides (mg %) | 211.2 ± 81.5 | 79.5 ± 9.2 | 44.5 ± 14.0 | 1.78 |
| Plasma Cholesterol (mg %) | 101.5 ± 15 | 84.0 ± 9.3 | 69.5 ± 9.7 | 1.2 |
| Plasma apo C-III (mg %) | 276 ± 31 | 63 ± 10 | 17 ± 14 |  |
| Plasma glucose (mg %) | 112 ± 5 | 114 ± 6 | 104 ± 4 | 1.1 |
| Plasma insulin (U/ml) | 28.9 ± 13.1 | 25.4 ± 5. | 24.2 ± 7.3 | 1.0 |

EXPERIMENT IV

Uncoupling of oxidative phosphorylation by compounds of formula I was evaluated in isolated liver cells loaded with JC-1 dye (as described by M. Reers et al., Meth. Enzymol. 260, 406 (1995))) and incubated in the presence of added compounds of formula I as specified. JC-1 fluorescence was determined by FACSCAN flow cytometry. While the cytosolic monomeric dye emits at 530 nm (when excited at 488 nm), the fluorescence of the intramitochondrial aggregated dye shifts to 590 nm. The 530/590 fluorescence ratio thus reflects the cytosolic/mitochondrial distribution of the dye as a result of the prevailing mitochondrial inner membrane potential of affected cells. The higher the 530/590 ratio the higher the extent of uncoupling and calorigenesis induced by added effectors. The results are shown in the following FIG. 1.

SUMMARY

The following conclusions were reached with regard to the biological effects of compounds of formula I:

(a) The active compounds are potent hypolipidemics. The overall hypolipidemic effect is based on activating plasma lipoproteins clearance resulting from decrease in plasma apo C-III.

(b) The active compounds are potent insulin sensitizers as reflected by plasma insulin concentrations required for maintaining euglycemia. Insulin sensitization may form the basis for using these compounds in the treatment of IGT/NIDDM.

(c) The active compounds induce increase in calorigenesis as a result of decrease in mitochondrial membrane potential. Uncoupling induced by these compounds may form the basis for using these compounds in the treatment of obesity.

(d) These compounds may offer an whollystic therapeutic approach for the Metabolic Syndrome. Their efficacy is far higher as compared with homologous $\beta,\beta'$-substituted,compounds.

EXAMPLES

Example 1

4,4,11,11-Tetramethyltetradecanedioic Acid

Ethyl bromoacetate (14.4 g, 0.094 mol) was added dropwise over 30 min to a stirred solution of 26.2 g (0.1 mol) of triphenylphosphine in 120 ml of benzene maintained at 35 38° C. After stirring for additional 12 h at room temperature the precipitate was filtered and washed twice with hexane to give 34.7 g (86%) of (carboethoxymethyl)-triphenylphosphonium bromide, m.p. 159 160° C. 115 ml of 10% aqueous sodium hydroxide was added dropwise with cooling at 5° C. to a stirred suspension of 118.4 g (0.276 mol) of the bromide in 500 ml of water and 200 ml of chloroform containing a small amount of phenolphthalein. Stirring was continued over 30 min. period without external cooling followed by adding 500 ml of chloroform to give clear layers. The aqueous layer was extracted three times with 100 ml of chloroform and the combined chloroform fractions were dried over sodium sulfate and concentrated in vacuo. Crystallization of the residue from 180 ml of 1:1 mixture of benzene and hexane gave 86.2 g (90%) of pure (carboethoxymethylene)triphenylphosphorane, m.p. 119 120° C.

Potassium carbonate (56 g) was added portionwise over 1 h to a stirred mixture of 68 g (0.94 mol) of freshly distilled isobutyraldehyde and 70 ml of 40% formalin under argon. During addition the temperature was kept at 10 15° C. The temperature was allowed to rise to 25° C. while stirring was further continued under argon for 12 h, followed by adding 100 ml water to the white suspension.

The mixture was extracted four times with 40 ml of chloroform and the combined extracts were dried over magnesium sulfate and concentrated in vacuo.

Distillation of the remaining liquid (solidified upon cooling) through a 20-cm

Vigreux column gave 93.0 g (97%) of 2,2-dimethyl-3-hydroxy-propanol, b.p. 83 860 C/15 Torr, m.p. 90 93° C.

A solution of 2,2-dimethyl-3-hydroxypropanal (22 g, 0.22 mol) and (carboethoxymethylene)triphenylphosphorane (75 g, 0.22 mol) in dry dichloromethane (150 ml) was refluxed for 46 h. The solvent was then evaporated and the crude product was distilled at 15 Torr through a very short column. The distillate was separated into two fractions by redistillation through a 40-cm Widmer column. The first fraction gave 22.3 g (60%) of ethyl trans-4,4-dimethyl-5-hydroxypent-2-enoate, b.p. 133 136° C./15 Torr, nD23 1.4641. 1H NMR (CDCl$_3$): (=1.10 [s, 6H, C(CH$_3$)$_2$], 1.25 (t, 3H, CH$_3$CH$_2$), 3.40 (s, 2H, CH$_2$), 3.80 (br. s, 1H, OH), 4.15 (q, 2H, CH$_2$CH$_3$), 5.80 (d, 1H, J=16 Hz, 3-H). Anal. Calad. for C$_9$H$_{16}$O$_3$: C, 62.76; H, 9.36. Found: C, 62.92; H 9.50.

Ethyl trans-4,4-dimethyel-5-hydroxpent-2-enote (8.6 g, 0.05 mol) in 100 ml of dichloromethane was added to a strred suspension of 70 g (0.27 mol) of chromium trioxide-pyridine complex in 900 ml of anhydrous dichloromethane. The insoluble black gum residue was washed thoroughly three times with 100-ml portions of ether. The combined organic solutions were passed through a column (3.5-cm, 25-cm) of Silicagel and the solvent was removed by distillation. Distillation of the residue oil through a 20-cm Widmer column gave 8.0 g (94%) of ethyl 4-methyl-4formylpent-2-enoate, b.p. 110 111° C./15 Torr, nD18 1.4605. 1H NMR (CDCl$_3$): (=1.30 [s, 6H, C(CH$_3$)$_2$], 1.45 (t, 3H, CH$_3$CH$_2$), 4.15 (q, 2H, CH$_2$CH$_3$), 5.85 (d, 1H, J=16 Hz, 3-H), 6.90 (d, 1H, J=16 Hz, 2-H), 9.45 (s, 1H, CHO). Anal. Calcd. for C$_9$H$_{14}$O$_3$: C, 63.51; H, 8.29. Found: C, 63.53; H, 8.38. 8.64 g (0.04 mol) of dibromobutane and five drops of formnic acid were added to a solution of 26.2 g (0.1 mol) of tiphenyiphosphine in 125 ml of dimethylformamide and the mixtu(e was refluxed for 3 h, then cooled and diluted with 150 ml of ether. The formed precipitate was filtered off, washed with ether and dried. The crude product was dissolved in 35 ml of methanol and precipitated with 80 ml of ether to yield 25.2 g (85.2% yield) of butane-1,4-bis (triphenylphosphonium)dibromide, m.p. 302 303° C.

Butane-1,4 bis(triphenyl-phosphonium)dibromide (13.4 g, 0.018 mol) (dried over phosphorus pentoxide at least for 3 days) and 600 ml of dry tetrahydrofuran (refluxed over lithium aluminum hydride and distilled at atmosphere pressure) were placed in a dry 1-L three necked flask flushied with argon and vigorously stirred under argon until a fine suspension was formed. Then 20 ml of 1.80 M solution of phenyllithium in ether was added dropwise during 1 h. The red solution was stirred at room temperature for 4 h and 6.12 g (0.036 mol) of ethyl 4-methyl-4-formylpent-2-enoate was added in one portion. The resulting white suspension was stirred at room temperature for 10 h and refluxed for 2 h. The reaction mixture was filtered and concentrated to yield a yellow viscous oil. After addition of 150 ml of ether to the oil, the solution was filtered once more.

The filtrate was concentrated to yield 5.82 g of an oil that was diluted with 30 ml of toluene and filtered through Al$_2$O$_3$ and Silicagel eluted by toluene. The solvent was evaporated to give 3.82 g of diethyl 4,4,11,1 1-tetramethyltetradeca-2,5,9,12-tetraenedionate.

A solution of 2.98 g (8.1 mmol) of diethyl 4,4,11,11-tetramethyltetradeca-2,5,9,12-tetraenedionate in 50 ml of methanol was hydrogenated with 0.2 g of Pt (prepared according to R. Adams, V. Voorhees and R. L. Shriner, Org. Synth. 8, 92 (1928)) until the tieoretical volume of hydrogen had been absorbed. The filtrate was concentrated to yield an oil that was diluted with 30 ml of toluene and filtered through Al$_2$O$_3$ and Silicagel eluted by toluene. The solvent was evaporated to give an oil. 25 ml of 25% NaOH solution and several drops of ethanol were added to the resulting oil, the resulting mixture was heated for 2 h at 50–60 ° C., acidified with conc. HCl and extracted with chloroform. The combined chloroform extracts were dried over sodium sulfate. After distilling off the solvent the residue was recrystallized from hexane to give 2.06 g (81%) of 4,4,11,11-tetramethyl-tetradecanedioic acid, m.p. 88–89° C. 1H NMR (CDCl$_3$): (=0.86 [s, 12H, —C(CH$_3$)$_2$], 1.05 1.38 (m, 16H, CH$_2$), 1.52 (m, 4H, 3,12-CH 2.30 (t, 4H, 2,13 CH$_2$), 9.50 (br. s, 2H, COOH). Anal. Calcd for C$_{18}$H$_{34}$O$_4$: C, 68.75; H, 10.90. Found: C, 68.95; H, 10.96.

Example 2

Diethyl 4,4,13,13-tetramethylhexadeca-2,5,11,14-tetraenedionate 4.88 g (0.02 mol) of 1,6-dibromohexane and one drop of formic acid were added to a solution of 13.1 g (0.05 mol) of triphenylphosphine in 60 ml of dimethylformamide and the mixture was refluxed for 3 h, then cooled and diluted with 20 ml of ether. The formed precipitate was filtered off, washed with 30 ml of ether and dried. The crude product was dissolved with heating in 25 ml of methanol and precipitated with 40 ml of ether to yield 12.6 g (82.0%) of hexane-1,6-bis(triphenylphosphonium) dibromide, m.p. 312–313° C.

Hexane-1,6 bis(triphenyl-phosphonium) dibromide (8.28 g, 0.011 mol) (dried over phosphorus pentoxide at least for 36 h) and 550 ml of dry tetrahydrofuran (refluxed over lithium aluminum hydride and distilled at atmosphere pressure) were placed in a dry 1-L three necked flask flushed with argon and vigorously stirred under argon until a fine suspension was formed. Then 17 ml of 1.375 M solution of phenyllithium in ether was added dropwise during 30 min.

The red solution was stirred at room temperature for 4 h and 3.6 g (0.021 mol) of ethyl 4-methyl-4-formylpent-2-enoate (prepared as in Ex. 1) in 50 ml of dry tetrahydro-furan was added in one portion. The resulting white suspension was stirred at room temperature for 10 h and refluxed for 2 h. The reaction mixture was filtered and concentrated to yield a yellow viscous oil. After addition of 100 ml of ether to the oil, the solution was filtered once more. The filtrate was concentrated to yield 3.7 g of an oil that was diluted with 20 ml of toluene, filtered through $Al_2O_3$ and then chromatographed on Silicagel column (100 g;

eluted by toluene) to yield 25 g (59% yield) of diethyl 4,4,13,13-tetramethylhexadeca-2,5,11,14tetra-enedionate. The ester gave one spot on TLC (Silufol UV 254, $CHCl_3$, Rf 0.75). 1H NMR ($CDCl_3$): (=1.18 [s,-12H, $C(CH_3)_2$], 1.25 (t, J=6 Hz, 6H, $CH_3CH_2$), 1.05 1.38 (m, 4H, 8,9-$CH_2$), 1.85 2.05 (m, 4H, 7,10-$CH_2$), 4.15 (q, 2H, J=6 Hz, $CH_2CH_3$), 5.22 5.30 (m, 4H, 5,6,11.12-CH), 5.75 (d, 2H, J=14 Hz, 3,14-CH), 7.05 (d, 2H, 2,15-CH).

Example 3

4.4,13,13-Tetramethylhexadecanedioic Acid

A solution of 5.43 g (0.014 mol) of Ex. 2 in 50 ml of methanol containing 0.3 g of Pt was hydrogenated and hydrolyzed as described in Ex. 1 to yield 3.52 g (74%) of 4,4,13,13-tetramethylhexadecanedioic acid. m.p. 85 86° C. 1H NMR ($CDCl_3$): (=0.86 [s, 12H, $C(CH_3)_2$], 1.05 1.38 (m, 20H, $CH_2$), 1.52 (m, 4H, 3,14-$CH_2$), 2.30 (t, 4H, 2.15-$CH_2$), 9.50 (br. s, 2H, COOH). Anal. Calcd. for $C_{20}H_{38}O_4$: C, 70.13; H, 11.18. Found: C, 70.07; H, 11.02.

Example 4

4,4,15,15-Tetramethyloctadecanedioic Acid 10.88 g (0.04 mol) of 1.8-dibromoctane and five drops of formic acid were added to a solution of 26.2 g (0.1 mol) of triphenylphosphine in 125 ml of dimethylformamide and the mixture was refluxed for 3 h, then cooled and diluted with 150 ml of ether. The formed precipitate was filtered off, washed with ether and dried. The crude product was dissolved in 35 ml of methanol and precipitated with 80 ml of ether to yield 27.1 g (85.2%) of octane-1,8-bis(triphenylphosphonium) dibromide, m.p. 255 257° C. 1H NMR ($CDCl_3$): (=0.7 1.3 [m, 12H, $(CH_2)_6$], 3.0–3.3 (m, 4H, 2$PCH_2$), 7.1–7.5 (m, 30H, 2$PPh_3$). Anal. Calcd. for $C_{44}H_{46}Br_2P_2$: Br, 20.06. Found: Br, 20.22.

Octane-1.8 bis(triphenyl-phosphonium)dibromide (14.34 g, 0.018 mol) (dried in a vacuum desiccator over phosphorus pentoxide at least for 10 days) and 400 ml of dry tetrahydrofuran (refluxed over lithium aluminum hydride and distilled at atmosphere pressure) were placed in a dry 1-L three necked flask flushed with argon and vigorously stirred under argon until a fine suspension was formed. Then 20 ml of 1.86 M solution of phenyllithium in ether was added dropwise during 30 min. The red solution was stirred at room temperature for 2.5 h and 6.12 g (0.036 mol) of ethyl 4-methyl-formylpent-2-enoate (prepared as in Ex. 1) was added in one portion. The resulting white suspension was stirred at room temperature for 14 h and refluxed for 1 h. The reaction mixture was filtered and concentrated to yield a yellow viscous oil. After addition of 150 ml of ether to the oil the solution was filtered once more. The filtrate was concentrated to yield 6.69 g of an oil that was diluted with 30 ml of toluene and filtered through $Al_2O_3$ and Silicagel eluted by toluene. The solvent was evaporated to give 4.33 g of diethyl 4,4,15,15-tetra-methyloctadeca-2,5,13,16-tetraenedionate.

A solution of 2.26 g (5.4 mmol) of diethyl 4,4,15,15-tetratnethyloctadeca-2,5,13,16-tetraenedionate in 50 ml of ethanol containing 0.5 g Ni (prepared according to H. Adkins, Org. Syntheses Coll. 3, 180 (1955)) was hydrogenated until the theoretical volume of hydrogen had been absorbed and filtered. The filtrate was processed as described in Ex. 1 to yield 1.24 g (62% yield) of acid, m.p. 71–72° C. 1H NMR ($CDCl_3$): (=0.86 [s, 12H, $C(CH_3)_2$], 1.05 1.38 (m, 24H, $CH_2$), 1.52 (m, 4H, 3,16-$CH_2$), 2.30 (t, 4H, 2,17-$CH_2$), 9.50 (br. s, 2H, COOH). Anal. Calcd. for $C_{22}H_{42}O_4$: C, 71.30; H, 11.42. Found: C, 71.35: H, 11.35.

Example 5

2,2,13,13-Tetramethyltetradecanedioic Acid 43 ml (80 mmol) of 1.88 N solution of butyllithium in hexane were added dropwise to 8.1 g (80 mmol) of dilsopropylamine in 60 ml of THF. After stirring during 30 min at the same temperature, 3.5 g (40 mmol) of isobutyric acid was added dropwise. The mixture was warmed gradually to room temperature and stirred for 3 h, then cooled to 15°C. again followed by adding 1,10-dibromodecane (4.5 g, 15 mmol) in one portion. After stirring for 3 h at room temperature the reaction was quenched by 40 ml of 12% hydrochloric acid while cooling with ice water. The aqueous layer was extracted with benzene, washed with water and dried over $MgSO_4$. After removing the solvent the residue crystallized. The product was recrystallized from hexane to yield 3.4 g (72%) of 2,2,13,13-tetramethyl tetradecanedioic acid, m.p. 86 87.5° C.

1H NMR ($CDCl_3$) delta 1.18 (s, 12H, $CH_3$), 1.20–1.32 (br. m, 16H, $CH_2$), 1.52 (br. t, 4H, β-$CH_2$).

Example 6

2,2,15,15-Tetramethylhexadecanedioic Acid 3.5 g (40 mmol) of isobutyric acid were added at 15° C. under Ar to a solution of lithium diisopropylamide prepared from 8.1 g (80 mmol) of diisopropylamine in 60 ml of THF and 38.3 ml (80 mmol) of 2.1 N hexane solution of butyllithium.

The mixture was stirred at room temperature for 3 h, and cooled again to 15° C. 3.3 g (10 mmol) of 1,12-dibromododecane were then added in one portion, the temperature was raised gradually to 20° C. and the reaction was stirred overnight. The reaction was quenched in ice by 12% hydrochloric acid, extracted with benzene, washed with water and dried. The product was crystallized from hexane to yield 2.6 g (71%) of 2,2,15,15-tetramethylhexadecanedioic acid, m.p. 90 91° C. Found %: C 69.75; H 11.14; Calcd %: C 70.13; H 11.18. 1H NMR ($CDCl_3$) delta 1.18 (s, 12H, CH3), 1.20–135 (br. m, 20H, CH2), 1.50 (br. t, 4H, β-CH2).

Example 7

2,2,17,17-Tetramethyloctadecanedioic Acid 1,14-Dibromotetradecane was prepared by adding HBr into a solution of 4.0 g (20.6 mmol) of 1,13-tetradecadiene and 0.5 g of benzoyl peroxide in benzene at room temperature. The mixture was stirred for two hours and chromatographed on $Al_2O_3$ (4 12 cm) with benzene eluent. 1,14 Dibromotetradecane was isolated and recrystallized from. hexane to yield 6.8 g (93.1%), m.p. 50° C. 2,2,17,17-Tetramethyloctadecanedioic acid was synthesized by adding dropwise 17.5 ml (30 mmol) of 1.72 N solution of butyllithium in hexane to 3.0 g (30 mmol) of diisopropyl-amine in 40 ml of THF in an Ar atmosphere at 15–5° C. Following 30 min the mixture was cooled to 20° C. and 1.3 g (15 mmol) of isobutyric acid were added. The temperature was gradually increased to 20 C. and stirring was continued for three hours. The reaction mixture was cooled again to −15° C. followed by adding the prepared 1,14-dibromotetradecane (0.2 g, 3.4 mmol) in one portion. The temperature was increased to 20° C. and the reaction was stirred overnight. The reaction was quenched in ice by 12% hydrochloric acid, extracted with benzene, washed with water and dried. The product was crystallized from hexane to yield 1.0 g (80%) of 2,2,17,17-tetramethyloctadecanedioic acid, m.p. 94 96° C. (from hexane). Found So: C 71.10; H 11.40. Calcd %: C 71.30; H 11.42. 1H NMR (CDC13) delta 1.18 (s, 12H, CH3), 1.25 (br. s, 24H, CH2), 1.51 (br. t, 4H, β-CH2).

What is claimed is:

1. A composition represented by the general fomula

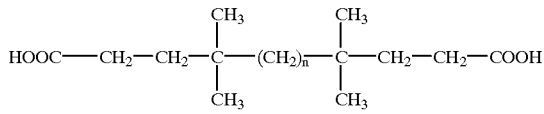

where $R_1$–Reach independently repersents an unsubstituted hydrocarbyl or heteroclyl radical;

where $R_3$ and $R_6$ independently represents hydrogen, hydroxyl, lower alkyl, chloro, bromo, cyano, nitro, lower alkoxy or triflouromethyl;

Q represents a diradical consisting of a linear chain of 4 to 14 carbon atoms, one or more of which may be replaced by heteroatoms, said chain being optionally substituted by inert substituents and one or more of said carbon or heteroatom chain members optionally forming part of a ring structure, and where one or both of the carboxyl groups can be substituted by an in vitro hydrolyzable physiologically acceptable substituent.

2. A compound according to claim 1, where $R_5$ and $R_6$ independently represent hydroxl, methyl, ethyl, methoxy or chloro.

3. A compound represented by the formula

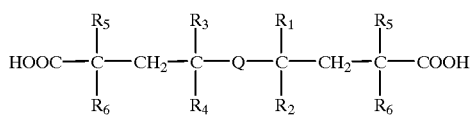

where n is an integer from 6 to 12, and their hydrolyzable functional derivatives.

4. A compound according to any of the claims 1 to 3 wherein the hydrolyzable derivative is a pharmaceutically acceptable inorganic or organic cation, ester, amide or anhydride of a lower alkanoic acid or an internal ester, amide or anhydride of such acid.

5. A compound according to claim 3, wherein the compound is 4,4,11,11-tetramethethyltetradecanedioic acid.

6. A compound according to claim 3, wherein the compound is 4,4,13,13-tetramethylboxadecanedioic acid.

7. A compound according to claim 3, wherein the compound is 4,4,15,15-tetramethyloctadecanedioic acid.

8. A pharmaceutical composition comprising as active ingredient a compound claimed in any of the claims 1,2,3, 5,6, and 7.

9. A pharmaceutical composition for the treatment of obesity, hyperlipidermia and maturity onset diabetes which comprises as active ingredient an effective amount of the compound claimed in any of the claims 1,2,3,5,6,8 and 7.

10. A pharmaceutical composition according to claims 8 and 9, wherein the amount of the active ingredient per unit dosage is from 50 to 500 mg.

* * * * *

UNITED STATES PATENT AND TRADEMARK OFFICE
CERTIFICATE OF CORRECTION

PATENT NO.    : 6,284,903 B1
DATED         : September 4, 2001
INVENTOR(S)   : Bar-Tana, Jacob It is certified that error appears in the above-identified patent and that said Letters Patent is hereby corrected as shown below:

Column 11,
Line 25, please change "$R_1$-Reach" to -- $R_1$ - R4 each --.
Line 26, please change "heteroclyl" to -- heterocyclyl --.
Line 27, please change "$R_3$" to -- $R_5$ --.
Line 29, please change "triflouromethyl" to -- trifluoromethyl --.

Column 12,
Line 2, please change "hydroxl" to -- hydroxyl --
Line 21, please change "-tetramethethyltetradecanedioic" to
-- -tetramethyltetradecanedioic --.
Line 23, please change "-tetramethylboxadecanedioic" to
-- -tetramethylhexadecanedioic --.

Signed and Sealed this

Sixteenth Day of July, 2002

Attest:

JAMES E. ROGAN
Attesting Officer
Director of the United States Patent and Trademark Office